(12) United States Patent
McKenna (10) Patent No.: US 9,277,888 B2
(45) Date of Patent: *Mar. 8, 2016

(54) PHOTON DENSITY WAVE PULSE OXIMETRY AND PULSE HEMOMETRY

(71) Applicant: Covidien LP, Mansfield, MA (US)

(72) Inventor: Edward M. McKenna, Boulder, CO (US)

(73) Assignee: Covidien LP, Mansfield, MA (US)

( * ) Notice: Subject to any disclaimer, the term of this patent is extended or adjusted under 35 U.S.C. 154(b) by 279 days.

This patent is subject to a terminal disclaimer.

(21) Appl. No.: 13/764,947

(22) Filed: Feb. 12, 2013

(65) Prior Publication Data

US 2013/0197331 A1    Aug. 1, 2013

Related U.S. Application Data

(63) Continuation of application No. 12/241,160, filed on Sep. 30, 2008, now Pat. No. 8,386,000.

(51) Int. Cl.
*A61B 5/1455* (2006.01)
*A61B 5/00* (2006.01)

(52) U.S. Cl.
CPC ............ *A61B 5/7228* (2013.01); *A61B 5/14551* (2013.01); *A61B 5/7203* (2013.01)

(58) Field of Classification Search
CPC ............... A61B 5/7228; A61B 5/7203; A61B 5/14551; A61B 5/1455; A61B 5/14546

USPC ................. 600/310, 322, 323, 336, 473, 476
See application file for complete search history.

(56) References Cited

U.S. PATENT DOCUMENTS

| 5,413,100 | A | 5/1995 | Barthelemy et al. |
| 5,555,855 | A | 9/1996 | Takahashi |
| 6,058,324 | A | 5/2000 | Chance |
| 6,192,260 | B1 | 2/2001 | Chance |
| 6,246,892 | B1 | 6/2001 | Chance |
| 2008/0139908 | A1 | 6/2008 | Kurth |
| 2011/0071373 | A1 | 3/2011 | Li et al. |

FOREIGN PATENT DOCUMENTS

| RU | 2038037 | 6/1995 |
| RU | 2040912 | 8/1995 |

OTHER PUBLICATIONS

Vasilis Ntziachristos, et al.; "Oximetry Based on Diffuse Photon Density Wave Differentials;" Medical Physics; Feb. 2000; pp. 410-421; vol. 27, No. 2; Am. Assoc. Phys. Med.; Melville, NY, US.

*Primary Examiner* — Eric Winakur (57) ABSTRACT

Present embodiments are directed to a system and method capable of modulating light to at least one modulation frequency selected based on at least one blood parameter of a medium being monitored to generate photon density waves in a medium, detecting relative amplitude changes and phase shifts in the photon density waves, and determining at least one blood parameter related to scattering particles in the medium based on the phase shifts.

19 Claims, 5 Drawing Sheets

PHOTON DENSITY WAVE PULSE OXIMETRY AND PULSE HEMOMETRY

RELATED APPLICATIONS

This application is a continuation of and claims the benefit of U.S. application Ser. No. 12/241,160, filed on Sep. 30, 2008, and entitled "System And Method For Photon Density Wave Pulse Oximetry And Pulse Hemometry" which is hereby incorporated by reference in its entirety.

BACKGROUND

This section is intended to introduce the reader to various aspects of art that may be related to various aspects of the present embodiments, which are described and/or claimed below. This discussion is believed to be helpful in providing the reader with background information to facilitate a better understanding of the various aspects of the disclosed embodiments. Accordingly, it should be understood that these statements are to be read in this light, and not as admissions of prior art.

Pulse oximetry may be defined as a non-invasive technique that facilitates monitoring of a patient's blood flow characteristics. For example, pulse oximetry may be used to measure blood oxygen saturation of hemoglobin in a patient's arterial blood and/or the patient's heart rate. Specifically, these blood flow characteristic measurements may be acquired using a non-invasive sensor that passes light through a portion of a patient's tissue and photo-electrically senses the absorption and scattering of the light through the tissue. Typical pulse oximetry technology currently utilizes two light emitting diodes (LEDs) and a single optical detector to measure pulse and oxygen saturation of a given tissue bed.

A typical signal resulting from the sensed light may be referred to as a plethysmograph waveform. Such measurements are largely based on absorption of emitted light by specific types of blood constituents. Once acquired, this measurement may be used with various algorithms to estimate a relative amount of blood constituent in the tissue. For example, such measurements may provide a ratio of oxygenated to deoxygenated hemoglobin in the volume being monitored. It should be noted that the amount of arterial blood in the tissue is generally time varying during a cardiac cycle, which is reflected in the plethysmographic waveform.

The accuracy of blood flow characteristic estimation via pulse oximetry depends on a number of factors. For example, variations in light absorption characteristics can affect accuracy depending on where the sensor is located and/or the physiology of the patient being monitored. Additionally, various types of noise and interference can create inaccuracies. For example, electrical noise, physiological noise, and other interference can contribute to inaccurate blood flow characteristic estimates. Some sources of noise are consistent, predictable, and/or minimal, while some sources of noise are erratic and cause major interruptions in the accuracy of blood flow characteristic measurements. Accordingly, it is desirable to enable more accurate and/or controlled measurement of physiologic parameters by providing a system and method that addresses inconsistencies in physiologic characteristics of patients and issues relating to noise.

BRIEF DESCRIPTION OF THE DRAWINGS

Advantages of present embodiments may become apparent upon reading the following detailed description and upon reference to the drawings in which.

DETAILED DESCRIPTION OF SPECIFIC EMBODIMENTS

Present embodiments relate generally to medical devices. More particularly, present embodiments relate to estimating physiological parameters related to blood in a patient based on detection of light wave characteristics after the associated light waves have been transmitted through the patient's tissue.

One or more embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Present embodiments relate to non-invasively measuring physiologic parameters corresponding to blood flow in a patient by emitting light into a patient's tissue with light emitters (e.g., lasers/LEDs) and photoelectrically detecting the light after it has passed through the patient's tissue. More specifically, present embodiments are directed to modulating the emitted light at high frequencies to generate resolvable photon density waves. Photon density waves may be described as progressively decaying waves of intensity. On a microscopic level, photons generated by a light source generally make random migrations in a scattering medium. However, the photons collectively form a photon density wave at a modulation frequency that moves away from the light source. Photon propagation is generally dictated by scattering and absorption in the medium through which the waves are moving. Like other waves, photon density waves undergo refraction, diffraction, interference, dispersion, attenuation, and so forth.

Phase changes and amplitude changes in the photon density waves after passing through a medium may be detected to facilitate measurement of changes in total scattering particles and absorber concentration, respectively, in the observed medium. Indeed, the phase of such waves may be sensitive to scattering and the amplitude of such waves may be sensitive to absorption. For example, detection of phase changes in the photon density waves generated by modulation at high frequency may correspond to total hemoglobin because the distance between waves may be shorter than an average absorption length of photons. Thus, detected variations in the phase may be predominantly due to the scattering coefficient and not absorption. In other words, the variation in phase may be predominantly due to the total number of scattering particles (e.g., total hemoglobin) in the observed medium and not merely a ratio of particles (e.g., oxygenated and deoxygenated hemoglobin) that absorb different frequencies of light. On the other hand, changes in the amplitude of the photon density waves may correspond to absorption of specific light frequencies (e.g. red or infrared light) in the observed volume, and, thus, a ratio of different types of particles (e.g., oxygenated and deoxygenated hemoglobin) in the probed medium.

In addition to the features set forth above, it should also be noted that present embodiments may relate to emitting multiple high frequency photon density waves in coordination with one another to focus on certain tissue areas (e.g., regions rich with pulsatile signals), to facilitate identification of noise artifacts, to address patient specific tissue characteristics (e.g., skin color and low blood oxygen saturation levels), and/or to reduce noise in general. For example, multiple photon density waves may be emitted in patterns such that the waves build on one another to focus intensity at certain points throughout a tissue bed. In a specific example, a tissue bed may be swept with combinations of emission frequencies to identify areas rich with pulsatile signals. Similarly, waves may be emitted such that the waves cancel one another out in a substantially noise-free environment. Thus, detection of the waves that have not been canceled out may be indicative of the presence of noise. Additionally, relative measurements may be utilized to identify and/or correct noise. For example, certain wave features may be detected at multiple detector locations and compared to one another to identify characteristics such as venous pulsation noise.

Figure 1:
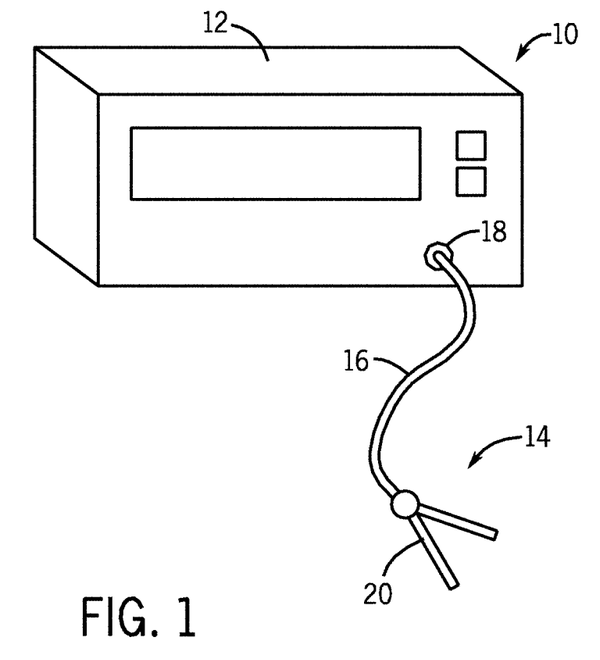
FIG. 1 illustrates a perspective view of a pulse oximeter system in accordance with present embodiments.

FIG. 1 illustrates a perspective view of a pulse oximetry system 10 in accordance with some embodiments. The system 10 includes a pulse oximeter or monitor 12 that communicatively couples to a sensor 14. The monitor 12 may include a display, a memory, a processor, and various monitoring and control features. The sensor 14 may include a sensor cable 16, a connector plug 18, and a sensor assembly or body 20 configured to attach to a patient (e.g., a patient's finger, ear, forehead, or toe). The system 10 may be utilized to observe the blood constituents of a patient's arterial blood to facilitate estimation of the state of oxygen exchange in the patient's body by emitting waves into tissue and detecting the waves after dispersion and/or reflection by the tissue. The amount of light that passes through the tissue and other characteristics of light waves may vary in accordance with the changing amount of certain blood constituents in the tissue and the related light absorption and/or scattering. For example, as with conventional pulse oximeter systems, the system 10 may emit light from two or more LEDs or lasers into pulsatile tissue and then detect the transmitted light with a light detector (e.g., a photodiode or photo-detector) after the light has passed through the pulsatile tissue. Such measurements may be utilized to estimate a percentage of blood oxygen saturation in the probed volume of blood. Additionally, in accordance with present embodiments, the system 10 may modulate the emitted light to generate photon density waves at a high frequency such that phase shifts may be detected that correlate predominantly to scattering particles in the probed volume of blood.

As generally indicated above, the system 10 may generate and detect light waves to facilitate non-invasive measurement of a patient's physiological characteristics. In embodiments, the system 10 may generate resolvable photon density waves and make relative measurements of certain detected wave characteristics after the waves have passed through a medium (e.g., a patient's tissue). The wave characteristics that may be measured in accordance with present embodiments may include characteristics that relate predominantly to absorption of the emitted light in the probed medium (e.g., amplitude change) and characteristics that relate predominantly to scattering in the probed medium (e.g., phase shift). It should be noted that, as will be discussed further below, the correlation of certain wave characteristic (e.g., amplitude and phase) measurements to certain medium characteristics (e.g., quantity of scattering particles and blood oxygen saturation) may be based on high frequency modulation of the system's light sources, which generate the resolvable photon density waves.

As indicated above, the system 10 may be utilized to make measurements that relate predominantly to scattering in the observed volume. More specifically, the system 10 may be utilized to make measurements relating to a total amount of scattering particles in the observed volume based on phase shifts detected in the emitted light waves. For example, the system 10 may emit light that is modulated at a high frequency (e.g., 50 MHz to 3.0 GHz) to generate resolvable photon density waves, and then measure the phase shift of these high frequency waves to facilitate estimation of a total number of scattering particles in the observed medium. Similarly, as set forth above, the system 10 may be utilized to make measurements that relate predominantly to absorption in an observed volume. For example, the system 10 may detect changes in AC and DC amplitudes of the resolvable photon density waves to facilitate detection of a ratio of certain constituents in the blood (e.g., a ratio of oxygenated to deoxygenated hemoglobin). It should be noted that the amplitude changes and phase shifts measured at a detection point may be considered relative to one or more points. For example, the amplitude and phase shifts measured at a detector may be considered relative to the associated values generated at the emitter.

Figure 2:
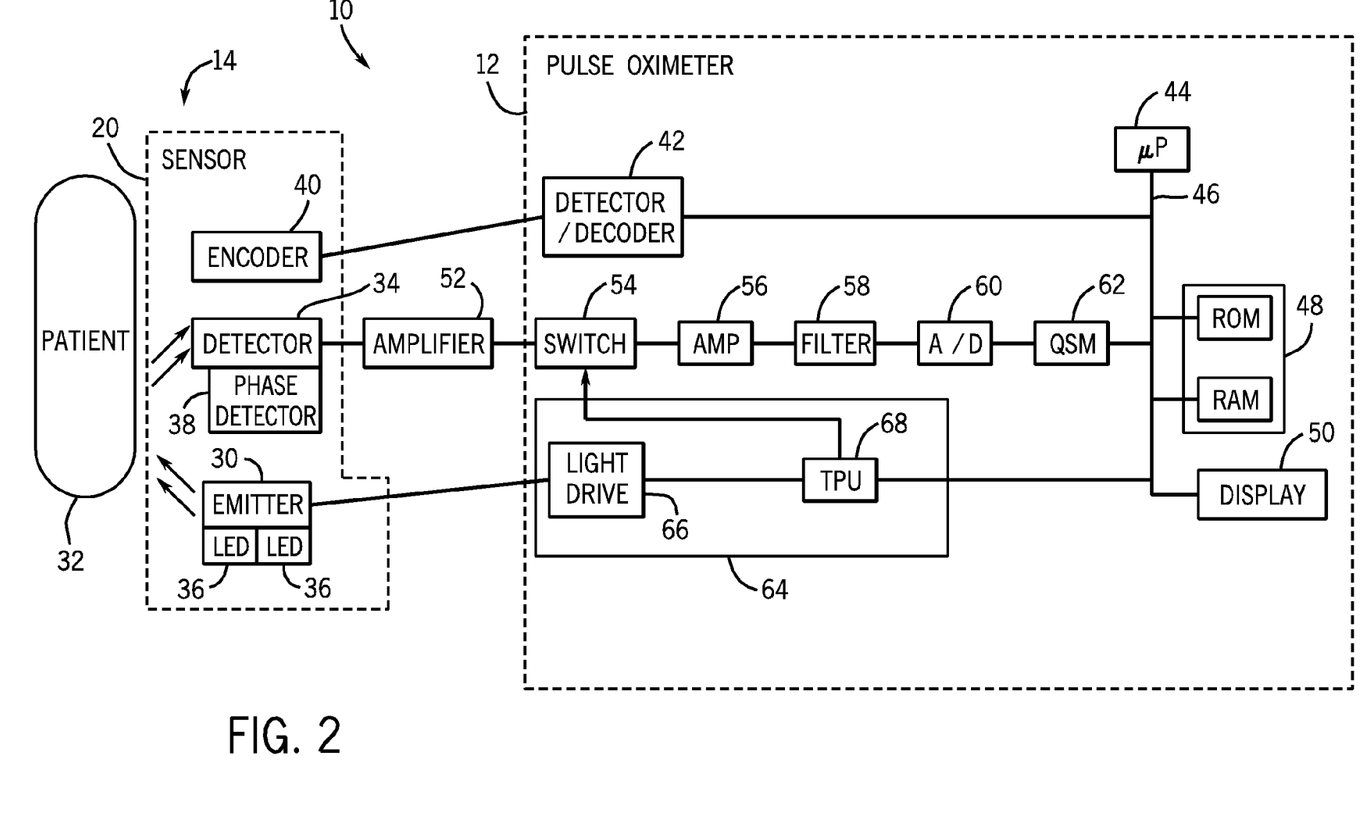
FIG. 2 illustrates a block diagram of a pulse oximeter system in accordance with present embodiments.

FIG. 2 is a block diagram of an embodiment of the pulse oximeter system 10 that may be configured to implement the embodiments of the present disclosure. As indicated above, the system 10 may include a monitor 12 and a sensor 14. The sensor 14 may be configured such that light from an emitter 30 can pass into a patient's tissue 32 when properly attached. Further, the sensor 14 may be configured such that after passing through the tissue 32, the dispersed light may be received by a photo-detector 34. The photo-detector 34 may then convert the received light into a photocurrent signal, which may then be provided to the monitor 12. It should be noted that in some embodiments, multiple sensors 14 may be employed. Further, in some embodiments, one or more sensors may each include multiple emitters and/or detectors. If multiple emitters are employed, it will generally be desirable for each of the emitters to include red and infrared (IR) light sources, such as LEDs 36, wherein each red and IR light source is configured to emit a wavelength that is within 10-20 nm of the other red or IR light source, respectively.

In some embodiments, in addition to the emitter 30 and the detector 34, the sensor assembly or body 20 may also contain various other features in accordance with present embodiments. For example, the sensor 14 may include a phase detector 38 capable of detecting phase shifts in photon density waves observed by the detector 34. While the phase detection feature 34 is positioned within the sensor assembly 20 in the illustrated embodiment, in some embodiments, the phase detection feature 34 may be located within the oximeter 12. Additionally, the sensor 14 may include an encoder 40 (e.g., a resistor or chip) which may be capable of providing signals indicative of the wavelength(s) of light received from the emitter 30 to allow the oximeter 12 to select appropriate calibration coefficients for calculating oxygen saturation. The data or signal from the encoder 40 may be decoded by a detector/decoder feature 42 in the oximeter 12.

In some embodiments, the oximeter 12 may include a microprocessor 44 coupled to an internal bus 46. Also connected to the bus 46 may be a memory 48 (e.g., RAM and/or ROM) and a display 50. Received signals from the detector 34 may be passed through a first amplifier 52, a switch 54, an analog multiplier 56, a low pass filter 58, and/or an analog-to-digital converter 60. The digital data may then be stored in a queued serial module (QSM) 62 for later downloading to the memory 48 as the QSM 62 fills up. In an embodiment, there may be multiple parallel paths of separate amplifier, filter, and A/D converters for multiple light wavelengths or spectra received, and/or for phase data generated by the phase detector 38. In one embodiment, a signal from the phase detector 38 may be processed in any suitable manner, and may be sent through a different data path than the signal from the detector 34, which may be configured to detect amplitude of the photon density waves. The received optical signal may be converted into an electrical signal at the detector 34. The electrical signal may then be amplified by the amplifier 52 and sent to a frequency mixer or analog multiplier (e.g., analog multiplier 56) to generate a signal that is proportional to a phase difference between a reference oscillator (not shown) and the received signal. Similarly, the AC and DC amplitudes of the received signal may be determined with peak detection circuits and low pass filters (e.g., filter 58).

As illustrated in the embodiment of FIG. 2, the emitter 30 may include the two LEDs 36. The LEDs 36 may receive modulated drive signals from the monitor 12 that activate the LEDs 36 and cause them to emit light at certain intervals. Thus, the monitor 12 may activate and deactivate the LEDs 36 at high frequencies that may facilitate measurements relating to scattering in the probed medium based on phase changes in emitted photon density waves. This modulation function may be performed by a modulator 64. The modulator 64 may include a hardware feature, a software feature, or some combination thereof. For example, a portion of the modulator 64 may be stored on the memory 48 and may be controlled by the processor 44. In the illustrated embodiment, the modulator 64 includes a light driver 66 and a time processing unit (TPU) 68 that cooperate to modulate the light emissions of the LEDs 36. The TPU 68, which may include a sine wave generator, may provide timing control signals to the light drive circuitry 66, which controls when the emitter 30 is activated, and if multiple light sources are used, the multiplexed timing for the different light sources. The TPU 68 may also control the gating-in of signals from the detector 34 through the first amplifier 52 and the switching circuit 54. These signals are sampled at the proper time, depending at least in part upon which of multiple light sources is activated, if multiple light sources are used.

In the illustrated embodiment, the modulator 64 is disposed in the monitor 12. However, in some embodiments the modulation function may be performed by a modulator disposed within the sensor 14. Indeed, it should be noted that in some embodiments, the features related to modulating and detecting the phase of the emitted light waves may be arranged within the system 10 to avoid potential interference. For example, high frequency modulation and detection features may be co-located within the sensor 14 to reduce the distance traveled by the signals, and, thus, reduce potential interference. Indeed, in a specific example, the sensor 14 may include a commercially available chip set for phase measurement and commonly available drive circuits (e.g., DVD R/W driver circuits) for high frequency modulation. Examples of such devices may include the AD8302 available from Analog Devices™ and the LMH6525 available from National Semiconductor™. In other embodiments the LEDs 36 may be positioned within the monitor 12 and light may be transmitted from the LEDs 36 in the monitor 12 to the sensor 14 via fiber optics to reduce potential interference.

Regardless of the modulator's location, in contrast to traditional pulse oximetry, which conducts measurements at sufficiently low frequencies (e.g., 1.5 KHz) to be considered DC, the modulator 64 may be configured to modulate the LEDs 36 at sufficiently high frequencies (e.g., approximately 50 MHz to 3.0 GHz) to cause resolvable photon density waves to propagate through the tissue 38. In some embodiments, the modulator 64 may be configured to sweep a range from 50 MHz to 2.4 GHz. In some embodiments, the modulator 64 may be configured to modulate between 100 MHz and 1 GHz or to sweep a range from 100 MHz to 1 GHz. Thus, present embodiments operate at much higher frequencies than the traditional pulse oximetry sampling frequency of 1 sample every 67 microseconds.

In some embodiments, for continuous modulation of the LEDs 36, resolvable amplitude and phase relationships of the photon density waves may be established at various positions from the emitter along the tissue bed 32. By modulating the light emitters at sufficiently high frequencies, the distance between photon density waves may be shorter than the average distance required for light to be absorbed. Thus, the phase changes in the photon density waves can be attributed predominantly to scattering and not absorption. Further, in view of this, it can be determined that detected phase changes correspond to a number of scattering particles in the probed medium. The frequency of the photon density waves is essentially locked to the initial light source input and the phase change is essentially locked to arterial pulsation and the introduction of scattering particles. Indeed, the variation in AC scattering to DC scattering measured by phase offset may yield information about the total arteriole volume probed.

For a modulation frequency where the product of the frequency and the mean time between absorption events is much larger than 1, the change in phase between two points located a distance r from each other on a tissue bed may be given by the relation, $$\Delta \phi = r \sqrt{\frac{\omega \mu'_s}{6c}},$$

where c is the speed of light, ω is the angular frequency of modulation, and $\mu'_s$ is the reduced scattering coefficient. The reduced scattering coefficient for a tissue bed is comprised of both blood and surrounding tissue components. It can be written as, $$\mu'_s\text{total} = V_{blood}\mu'_s\text{blood} + V_{tissue}\mu'_s\text{tissue}.$$

The time varying component of this equation at a single wavelength will generally be only the portion due to arterial blood. The time varying component of this equation at a second wavelength will allow for the deconvolution of the scattering coefficient. The scattering coefficient for blood is related to the hematocrit (HCT) through the relation, $$\mu'_s\text{blood} = \sigma'_s(1-g)(HCT/V_1)(1-HCT)(1.4-HCT),$$

where g is the anisotropy factor, σ is the scattering cross section of an erythrocyte, Vi is the volume of an erythrocyte and HCT is the hematocrit.

Accordingly, when the modulator 64 operates at a high enough frequency, measured phase changes in the photon density waves may be utilized to calculate a number of scattering particles in the observed volume. For example, the monitor 12 may be configured to receive phase shift and/or amplitude data from the sensor 14 and calculate a value related to a quantity of scattering particles in the probed tissue for display on the monitor 12. Specifically, the monitor 12 may include instructions or an algorithm stored on the memory 48 and configured to perform such calculations.

Figure 3A:
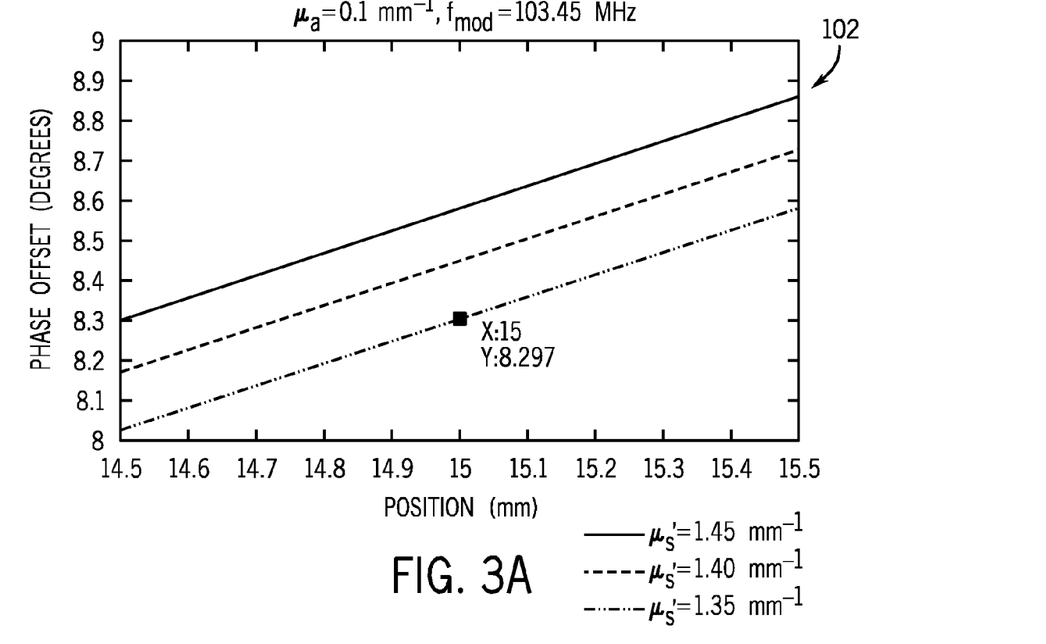
FIGS. 3A and 3B illustrate a pair of graphs that represent simulations of phase changes in photon density waves modulated at high frequency, wherein the phase changes are due to scattering in accordance with present embodiments.
Figure 3B:
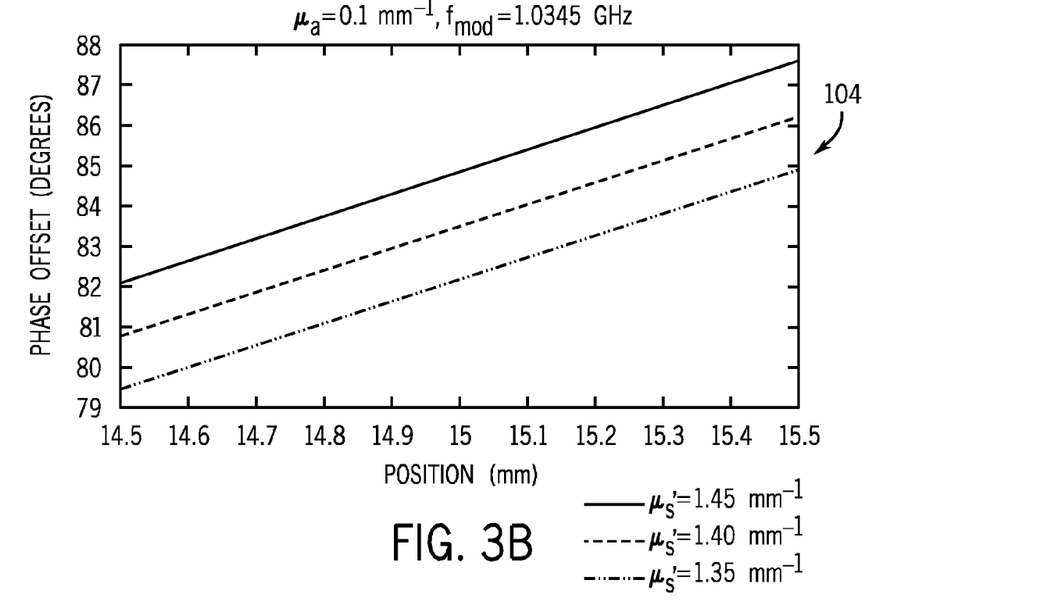

As an example of the correlation of phase change measurements of photon density waves modulated at high frequency to a number of scattering particles in the probed medium, FIG. 3 includes a pair of graphs that represent simulations of phase changes due to scattering at two different frequencies. Specifically, FIG. 3 includes a first graph 102 and a second graph 104 that represent simulations of phase change (measured in degrees) due to scattering variation of an arterial pulse (Hemoglobin 15 g/dL) for photon density waves at 890 nm that are modulated with a frequency of 103.4 MHz and 1.034 GHz, respectively. It should be noted that the increase in frequency from 103.4 MHz in the first graph 102 to 1.034 GHz in the second graph 104 results in a phase change of approximately 3-4 degrees. This change correlates to the reduction in distance between the wave fronts of the photon density waves. In other words, because the distance between waves is reduced even further from the 103.4 MHz modulation rate (first graph 102) to the 1.034 GHz modulation rate (second graph 104) and there is less opportunity for absorption, the phase change of the higher modulation rate corresponds more specifically to scattering. In some embodiments, a range of frequencies between those shown in FIGS. 3 and 4 may be swept through to profile the characteristics of the tissue at different photon density wave frequencies.

Scattering may be quantified based on phase change. Specifically, as set forth above, a modulation frequency where the product of the frequency and the mean time between absorption events is much larger than 1, the change in phase between two points may be given by the relation, $$\Delta \phi = r \sqrt{\frac{\omega \mu'_s}{6c}}.$$

Changes in phase due to arterial pulsation may be directly related to the change in scattering coefficient of the medium which is due to the change in the concentration of the number of erythrocytes. It should be noted that a second method for correlating the scattering changes from the phase could involve a calibration curve determined from tissue phantoms or clinical data.

Figure 4:
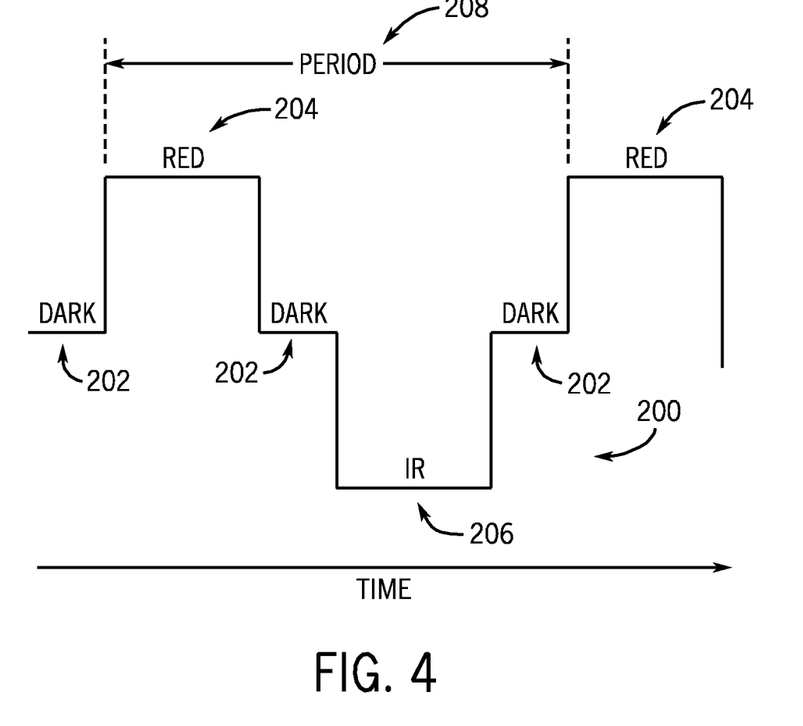
FIG. 4 illustrates an example of a source modulation signal in accordance with present embodiments.

FIG. 4 illustrates an example of a source modulation signal as driven by cross-coupled LEDs in accordance with some embodiments. Specifically, FIG. 4 illustrates a control signal 200 that may be generated by the modulator 64 to activate and/or deactivate an emitter including red and IR light sources, such as the LEDs 36. In other embodiments, separate modulators may be utilized for each light source and/or additional light sources. Indeed, when multiple emitters are utilized, each emitter may be modulated by a separate modulator.

In the illustrated embodiment, the control signal 200 is representative of dark intervals 202, intervals of power 204 being supplied to a red LED, and intervals of power 206 being supplied to an IR LED over time. Further, the control signal 200 has a period designated by reference number 208. This period 208 may be adjusted such that each of the LEDs 36 may be modulated with a desired frequency (e.g., approximately 100-1000 MHz) to generate photon density waves. Such adjustments to the modulation frequency may facilitate detection of phase shifts in the photon density waves, and, thus, variations in scattering based on such phase shifts. As may be appreciated by those of ordinary skill in the art, the control signal 200 may be adjusted or modified for different scenarios. For example, the control signal 200 may be adjusted to be generally sinusoidal, adjusted to include various intensity levels, and so forth. The sinusoidal nature of the wave may be controlled by a wave generator and the intensity levels may be adjusted by providing more power and/or by reducing dark intervals and increasing the length of time that light is emitted.

As indicated above, the phase of the photon density waves may be sensitive to changes in the scattering coefficient, while the amplitude of the photon density waves may be sensitive to the concentration of absorbers in the medium. Specifically, with regard to amplitude measurements, the AC amplitude and DC amplitude may yield information about absorption in the volume. Thus, detection of amplitude changes in the photon density waves may be utilized to calculate absorber concentration values in the observed medium, such as blood oxygen saturation values. Such calculations may be made using the standard ratio of ratios (i.e., ratrat) technique for the constant and modulated values of the photon density wave amplitudes at two wavelengths. Once the ratio of ratios values is obtained, it may be mapped to the saturation from clinical calibration curves.

With regard to phase shift measurements, when the wavelength of the photon density waves get below that of the mean absorption coefficient, the phase becomes almost exclusively a function of the scattering coefficient. While dependent upon the tissue bed being probed, this is generally believed to occur at a modulation frequency in the range of approximately 500 MHz. Thus, the phase shift measurement may yield information about the number of erythrocytes or red blood cells in the local probed volume. The HCT discussed above is proportional to the number of erythrocytes. Accordingly, by sweeping frequencies, a multi-parameter output may be obtained that relates to standard pulse oximetry measurements as well as the puddle hematorcit.

The amplitude and phase at a given frequency may be proportional to the scattering and absorption coefficient at a given wavelength until the product of the frequency and the mean time between absorption events is much larger than 1. When the product of the frequency and the mean time between absorption events is much larger than 1, the amplitude is a function of the absorption and phase is only a function of the scattering. Thus, a frequency sweep may be used to reduce the error in the determination of a single value of reduced scattering coefficient for the blood and a single value of absorption coefficient. Indeed, in some embodiments, the amplitude and phase information may be utilized together to yield a value of total hemoglobin per unit volume.

In some embodiments, by modulating the light sources at a sufficient frequency, and, thus, facilitating a detectable phase shift that corresponds to scattering particles, present embodiments may provide an extra degree of certainty for blood flow parameter measurements. Indeed, the detected amplitude for the photon density waves may be utilized to calculate traditional pulse oximetry information and the phase may be utilized to confirm that such values are correct (e.g., within a certain range of error). For example, the amplitude information may be utilized to calculate a blood oxygen saturation ($SpO_2$) value and empirical data may indicate that a particular $SpO_2$ value should correspond to a particular phase variation at a given frequency. In other words, there may be a certain phase change that should accompany a given increase in absorber observed as a change in amplitude. Various algorithms (e.g., learning based algorithms such as support vector machines, cluster analysis, neural networks, and PCA) based on the measured phase shift and amplitude change may be compared to determine if the amplitude shift and phase shift correlate to a known $SpO_2$. If both the measured amplitude shift and phase shift correlate to a known $SpO_2$, the measured $SpO_2$ value may be deemed appropriate and displayed or utilized as a correct $SpO_2$ value. Alternatively, if the measured amplitude shift and phase shift do not agree, the calculated $SpO_2$ value may be identified as being corrupt or including too much noise and, thus, be discarded.

Figure 5:
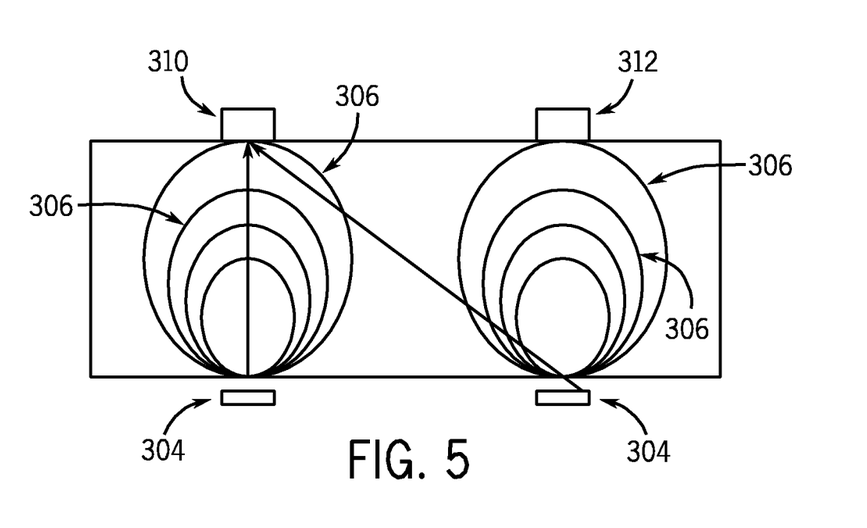
FIGS. 5, 6, and 7 include representative diagrams of a multiple emitter and/or detector arrangements being utilized in conjunction with one another in accordance with present embodiments.
Figure 6:
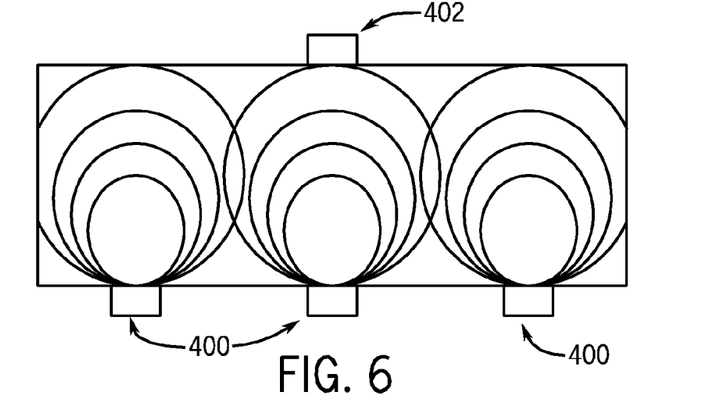
Figure 7:
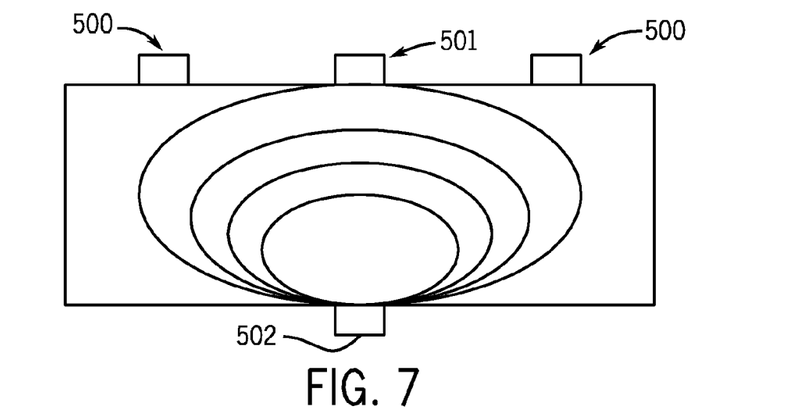

In some embodiments, as illustrated by FIGS. 5-7, multiple emitter and/or detector arrangements may be utilized in conjunction with one another. Specifically, FIG. 5 illustrates a first emitter 302 and a second emitter 304, wherein each of the emitters 302, 304 includes a red and an IR light source (e.g., LED). Waves 306 represent photon density waves propagating through tissue from the emitters 302, 304 to a first detector 310 and a second detector 312. As will be understood by one of ordinary skill in the art, because the multiple emitters are generating separate waves in the same tissue bed, the waves can be made to interfere with one another by adjusting the modulation frequencies of each emitter 302, 304. Accordingly, multiple emitters may be utilized to steer intensities through the tissue and adjust intensity patterns in the tissue. For example, the phase of the photon density waves could be adjusted in such a way as to completely cancel out any signal at the first detector 310. Thus, if the first detector 310 detects a signal, it may be an indication of noise.

FIG. 6 illustrates an embodiment including multiple emitters 400 and a single detector 402. This embodiment may be utilized to generate an adaptive constructive/destructive interference pattern in the tissue bed by adjusting the relative phases of the emitters (at a given wavelength) that would allow for the measurement of local tissue components. These would be visible in the phase and amplitude changes determined by the single detector.

In other embodiments utilizing multiple emitters, the interference of photon density waves may facilitate sweeping photon density waves through a probed volume by changing the relative phase between the emitters. For example, such techniques may be utilized to establish a "phased array" of photon density waves for use in pulse oximetry and hemometry techniques. Indeed, such a "phased array" technique may facilitate identification of regions rich with pulsatile signals in the probed tissue and/or calibration of a sensor through the interference of photon density waves. For example, the phases of individual waves may be controlled to determine the intensity profile within the medium.

It may be desirable to detect regions rich with pulsatile signals to facilitate obtaining a strong pulsatile signal. For example, it may be desirable to focus on a specific location in tissue that includes an artery or even a specific portion of the artery. Periodic sweeps may be performed to insure that the focus remains on the pulsation-rich regions. Further, such a technique may define an adaptive measurement system that may be utilized to identify regions of low saturation and/or regions in the probed tissue where blockage may result in anemic conditions. Additionally, it is believed that the use of multiple emitters may facilitate adaptation of the sensor to different physiological variations between patients, such as different skin and/or tissue characteristics.

FIG. 7 illustrates an embodiment including multiple detectors 500 and a single emitter 502. This embodiment may be utilized to identify non-physiological artifact. Each of the multiple detectors 500 may have a different phase and amplitude relationship with respect to each other. Uncorrelated changes in phase and amplitude between the multiple detectors 500 would result in a non-physiological artifact such as noise artifact, sensor off, and so forth.

The inclusion of multiple detectors around a tissue bed may facilitate detection of and/or compensation for a variety of noise artifacts that typically plague existing pulse oximetry technologies. Indeed, for a given wavelength, a time-varying phase and amplitude relation between multiple detectors may be established which is correlated to arterial pulse. The phase and amplitude information may form a phase space that yields a bounded parameter space for a single wavelength that contains physiological measurements. Noise artifacts will typically lie outside of this bounded area, as will be discussed in further detail below. Further, the addition of a second wavelength may facilitate formation of a 4-dimensional physiological measurement space that facilitates noise artifact reduction due to constraints of decision planes in the hyperspace. Correlated phase and amplitude changes for a single wavelength are bounded by physiological parameters such as arteriole density, realistic hematocrit numbers, and so forth. At a single wavelength, these bounds result in bounds on the detected amplitude and phase in a 2D space. These same bounds are applicable for a second wavelength. The 4 factor correlation (phase(wavelength1), phase(wavelength2), amplitude(wavelength1), amplitude(wavelength2)) is bounded by physiological factors in a linked 4D space. The bounds can be drawn as hyperplanes in that space. For example, cluster analysis, Neural Networks, and partial least squares (PLS) algorithms may be used to generate the decision planes and compensate for a variety of noise artifact.

Figure 8:
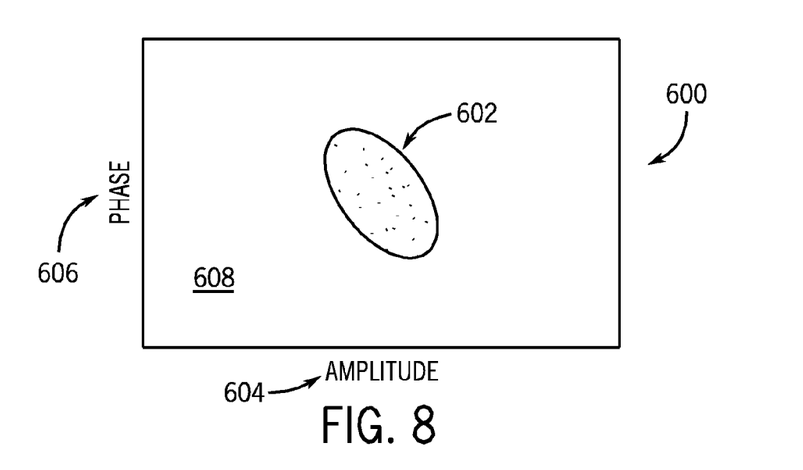
FIG. 8 illustrates a 2-dimensional plot that represents a physiological state characterized by amplitude and phase shifts in accordance with present embodiments.

In some embodiments, and as an example, FIG. 8 includes a 2-dimensional plot 600 that represents a physiological state 602 characterized by amplitude 604 and phase shifts 606. Once phase shift and/or amplitude data has been properly characterized based on empirical data, certain correlations may be indicative of a change in pressure (e.g., a sensor is attached too tightly), a certain area of tissue being subject to exsanguination, a sensor being off, noise being present, and so forth. The plot 600 is representative of a single wavelength at a given frequency. Thus, multiple wavelengths at a given frequency would each have this type of physiological space for expected amplitude and phase variation. Noise artifact 608 will generally lie outside of this bounded parameter space or physiological regime. Accordingly, if a measurement falls outside of the physiological regime, it may be discarded as including too much noise. When a measurement is discarded, it may be replaced with the previous measurement or some combination of historical values. For example, historical values may be averaged using an averaging routine to provide a replacement for the noisy current measurement value.

While the embodiments of the present disclosure may be susceptible to various modifications and alternative forms, specific embodiments have been shown by way of example in the drawings and will be described in detail herein. However, it should be understood that the present embodiments are not intended to be limited to the particular forms disclosed. Rather, present embodiments are to cover all modifications, equivalents and alternatives falling within the spirit and scope of present embodiments as defined by the following appended claims.

What is claimed is:

1. A monitoring system, comprising:
an emitter configured to emit light into tissue;
a modulator configured to modulate the light to at least one modulation frequency selected based on at least one blood parameter of the tissue being monitored to generate photon density waves in the tissue;
a detector configured to detect characteristics of the photon density waves comprising phase shifts;
a processor configured to determine a value of the at least one blood parameter of the tissue based on at least the phase shifts, and to calculate an estimated number of scattering particles in the tissue based on detected phase shifts.

2. The system of claim 1, wherein the modulator is configured to modulate the light to generate a first photon density wave of a first modulation frequency selected based on at least one absorbing property of the tissue, and wherein the modulator is configured to modulate the light to generate a second photon density wave of a second modulation frequency selected based on at least one scattering property of the tissue.

3. The system of claim 1, wherein the modulator is configured to modulate the light above approximately 50 MHz and below approximately 3 GHz.

4. The system of claim 1, comprising a plurality of emitters, wherein the modulator is configured to modulate light from the plurality of emitters to sweep the tissue with a plurality of modulation frequencies.

5. The system of claim 1, wherein the modulator comprises a DVD R/W driver circuit.

6. The system of claim 1, comprising a plurality of emitters configured to establish a phased array and comprising a second calculation component configured to utilize the phased array to identify a region of the tissue rich with pulsatile signals or a region of the tissue with low saturation.

7. The system of claim 1, comprising the detector configured to detect characteristics of the photon density waves comprising amplitude changes, and comprising a noise detection feature configured to identify noise artifacts based on a predefined range of calculated values based on the amplitude changes and phase shifts.

8. The system of claim 1, wherein the modulator is configured to establish a phased array of photon density waves for use in pulse oximetry and hemometry techniques.

9. A method, comprising:
modulating light to at least one modulation frequency selected based on at least one blood parameter of a medium being monitored to generate photon density waves in the medium;
detecting phase shifts in the photon density waves;
determining a value of the at least one blood parameter related to the scattering particles in the medium based on the phase shifts; and
calculating an estimated number of scattering particles in the tissue based on detected phase shifts.

10. The method of claim 9, comprising modulating multiple light emissions to generate a phased array of photon density waves.

11. The method of claim 10, comprising identifying regions rich with pulsatile signals based on the phased array of photon density waves.

12. The method of claim 10, comprising identifying regions of low saturation based on the phased array of photon density waves.

13. The method of claim 10, comprising modulating the light to generate a first photon density wave of a first modulation frequency selected based on at least one absorbing property of the tissue, and modulating the light to generate a second photon density wave of a second modulation frequency selected based on at least one scattering property of the tissue.

14. A monitoring system, comprising:
an emitter configured to emit light from a plurality of light sources into a medium;
a modulator configured to modulate the light from the plurality of light sources at different frequencies selected based on at least one blood parameter of the medium being monitored to generate photon density waves;
a processing system configured to coordinate the modulation of the plurality of light sources to establish coordinated wave characteristics; and
the processing system configured to determine a value for the at least one blood parameter of the medium based on at least detection of relative characteristics of the photon density waves after passing through the medium, and to calculate an estimated number of scattering particles in the tissue based on detected phase shifts.

15. The method of claim 14, wherein the processing system is configured to identify noise based on whether the coordinated wave characteristics are within a predefined physiologic regime.

16. The method of claim 14, wherein the coordinated wave characteristics comprise focused wave intensity in a specified region of the medium.

17. The method of claim 14, wherein the modulator is configured to sweep the medium with a plurality of modulation frequencies to facilitate calibration.

18. One or more non-transitory computer-readable media having stored thereon program instructions to facilitate the monitoring of blood parameters, wherein the program instructions, when executed by a computing system, direct the computing system to at least:
control modulation of light to at least one modulation frequency selected based on at least one blood parameter of tissue to generate photon density waves in a medium;
facilitate detection of phase shifts in the photon density waves;
identify a value of the at least one blood parameter related to the scattering particles in the medium based on the phase shifts; and
calculate an estimated number of scattering particles in the tissue based on detected phase shifts.

19. The one or more non-transitory computer-readable media of claim 18, wherein the program instructions further direct the computing system to calculate a value related to a number of scattering particles in the medium based on at least the phase shifts.

* * * * *